(12) United States Patent
Jung et al.

(10) Patent No.: US 6,538,090 B2
(45) Date of Patent: Mar. 25, 2003

(54) ORGANIC ANTI-REFLECTIVE POLYMER AND METHOD FOR MANUFACTURING THEREOF

(75) Inventors: Min-Ho Jung, Gyunggi-do (KR); Sung-Eun Hong, Gyunggi-do (KR); Ki-Ho Baik, Gyunggi-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 0 days.

(21) Appl. No.: 10/095,417

(22) Filed: Mar. 11, 2002

(65) Prior Publication Data

US 2002/0136834 A1 Sep. 26, 2002

Related U.S. Application Data

(62) Division of application No. 09/602,655, filed on Jun. 22, 2000, now Pat. No. 6,388,039.

(30) Foreign Application Priority Data

Jun. 22, 1999 (KR) .............................. 99-23382

(51) Int. Cl.$^7$ .............................. C08F 220/12
(52) U.S. Cl. .................... 526/329.6; 526/273; 526/311; 526/312; 526/326; 560/4; 560/5; 560/19
(58) Field of Search .................. 560/4, 5, 19; 526/273, 526/311, 312, 326, 329.6

(56) References Cited

U.S. PATENT DOCUMENTS

| | | |
|---|---|---|
| 4,424,270 A | 1/1984 | Erdmann et al. |
| 4,822,718 A | 4/1989 | Latham et al. |
| 5,525,457 A | 6/1996 | Nemoto et al. |
| 5,674,648 A | 10/1997 | Brewer et al. |

FOREIGN PATENT DOCUMENTS

| | | |
|---|---|---|
| EP | 0 277 038 A2 | 1/1988 |
| WO | WO00/01752 A1 | 1/2000 |

*Primary Examiner*—Helen L. Pezzuto
(74) *Attorney, Agent, or Firm*—Townsend and Townsend and Crew LLP

(57) ABSTRACT

Polymers are disclosed having the following formula 1 or 2:

(chemical formula 1)

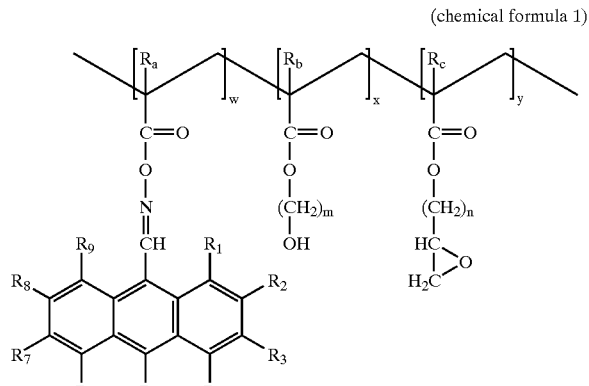

(chemical formula 2)

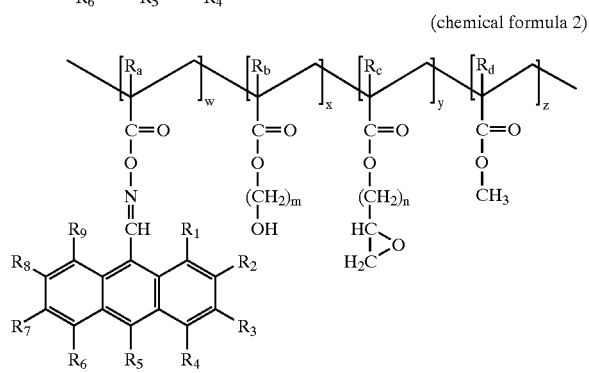

Polymers of the present invention can be used as an ARC material useful for submicrolithography processes using 248 nm KrF, 193 nm ArF and 157 nm $F_2$ lasers. The polymers contain a chromophore substituent that exhibits sufficient absorbance at the wavelengths useful for the submicrolithography process. The ARC prevents back reflection of light from lower layers and the alteration of the CD by diffracted and reflected light from the lower layers. The ARC also eliminates standing waves and reflective notching due to the optical properties of lower layers on the wafer and to changes in the thickness of the photosensitive film applied thereon, thereby resulting in the stable formation of ultrafine patterns suitable for 64M, 256M, 1 G, 4 G and 16 G DRAMs and a great improvement in the production yield.

12 Claims, No Drawings

ORGANIC ANTI-REFLECTIVE POLYMER AND METHOD FOR MANUFACTURING THEREOF

CROSS-REFERENCES TO RELATED APPLICATIONS

This application is a divisional of Ser. No. 09/602,655, filed on Jun. 22, 2000, now U.S. Pat. No. 6,388,039 B1.

BACKGROUND OF THE INVENTION

1. Field of the Invention

The present invention relates to an organic anti-reflective coating ("ARC") material which allows the stable formation of ultrafine patterns suitable for 64M, 256M, 1 G, 4 G and 16 G DRAM semiconductor devices. More particularly, the present invention relates to an organic anti-reflective coating material which contains a chromophore with high absorbance at the wavelengths useful for submicrolithography. A layer of said anti-reflective material can prevent the back reflection of light from lower layers of the semiconductor chip, as well as eliminate the standing waves caused by light and thickness changes of the photoresist layer itself, while conducting a submicrolithographic process using a 248 nm KrF, 193 nm ArF or 157 nm $F_2$ laser. Also, the present invention is concerned with an anti-reflective coating composition comprising such a material, an anti-reflective coating made therefrom and a preparation method thereof.

2. Description of the Prior Art

During a submicrolithographic process, one of the most important processes for fabricating highly integrated semiconductor devices, there inevitably occur standing waves and reflective notching due to the optical properties of lower layers on the wafer and to changes in the thickness of the photosensitive film applied thereon. In addition, the submicrolithographic process generally suffers from a problem of the CD (critical dimension) being altered by the diffracted light and reflected light from the lower layers.

To overcome these problems, it has been proposed to introduce a film, called an anti-reflective coating, between the substrate and the photosensitive film to prevent light reflection from the lower layer. Generally, anti-reflective coatings are classified into "organic" and "inorganic" by the materials used and into "absorption" and "interference" by the mechanisms involved. In microlithographic processes using an I-line light source (365 nm in wavelength), inorganic anti-reflective coatings are usually used, for example TiN or amorphous carbon coatings are applied when advantage is taken of an absorption mechanism, and SiON coatings are applied when an interference mechanism is desired. The SiON anti-reflective coatings are also adapted for submicrolithographic processes which uses KrF light sources.

Recently, extensive and intensive research has been and continues to be directed to the application of organic anti-reflective coatings for such submicrolithography. In view of the present development status, organic anti-reflective coatings, to be useful, must satisfy the following fundamental requirements:

First, peeling of the photoresist layer due to dissolution in solvents should not take place when conducting a lithographic process with an organic anti-reflective coating. In this regard, the organic anti-reflective coating materials have to be designed so that their cured films have a cross-linked structure without producing by-products.

Second, there should be no migration of chemical materials, such as amines or acids, into and from the anti-reflective coatings. If acids are migrated from the coatings, the photosensitive patterns are undercut while the egress of bases, such as amines, causes a "footing" phenomena.

Third, faster etch rates should be realized in the anti-reflective coatings than in the upper photosensitive film, allowing an etching process to be conducted smoothly with the photosensitive film serving as a mask.

Finally, the organic anti-reflective coatings should be as thin as possible while playing an excellent role in preventing light reflection.

As varied as anti-reflective coatings are, those which are satisfactorily applied to submicrolithographic processes using ArF light have not been found, thus far. As for inorganic anti-reflective coatings, there have been reported no materials which can control interference at the wavelength of ArF light, that is, 193 nm. As a result, active research has been conducted to develop organic materials which can form superb anti-reflective coatings. In fact, in most cases of submicrolithography, the coating of photosensitive layers is necessarily accompanied by the coating of organic anti-reflective layers which prevent the standing waves and reflective notching occurring upon light exposure and eliminate the influence of back diffraction and reflective light from lower layers. Accordingly, the development of such anti-reflective coating materials showing high absorption properties at specific wavelengths is one of the hottest and most urgent issues in the art.

SUMMARY OF THE INVENTION

The present invention overcomes the problems encountered in the prior art and provides a novel organic compound which can be used in an anti-reflective coating for submicrolithography processes using 193 nm ArF and 248 nm KrF lasers.

The present invention provides a method for preparing an organic compound which prevents the diffusion and reflection caused by light exposure in submicrolithography process.

The present invention further provides an anti-reflective coating composition containing such a diffusion/reflection-preventive compound and a preparation method therefor.

The present invention also provides an anti-reflective coating formed from such a composition and a preparation method therefor.

The present invention pertains to acrylate polymer resins (also referred to herein as "polymers" or "resins") which can be used as an anti-reflective coating. The polymer resins contain a chromophore which shows high absorbance of light having wavelengths of 198 nm and 248 nm. In addition, a cross-linking mechanism between alcohol groups and other functional groups is introduced into the polymer resins, so that a cross-linking reaction takes place when the coatings of the polymer resins are "hard baked," i.e., heated at a temperature of 100–300° C. for 10–1,000 seconds. As a result, a great improvement can be effected in the formation, tightness and dissolution properties of the anti-reflective coatings. Particularly, maximal cross-linking reaction efficiency and storage stability are realized in the practice of the present invention.

The anti-reflective coating resins of the present invention have superior solubility in all hydrocarbon solvents, in order to form a coating composition, yet are of such high solvent resistance after hard baking that they are not dissolved in any solvent at all. These advantages allow the resins to be coated without any problem to form an anti-reflective coating which prevents undercutting and footing problems when images are formed on the overlying photosensitive layer. Furthermore, coatings made of the acrylate polymers of the invention are higher in etch rate than the photosensitive film coatings, thereby improving the etch selection ratio therebetween.

DETAILED DESCRIPTION OF THE INVENTION

The acrylate polymer resins according to the present invention are represented by the following chemical formulas 1 and 2:

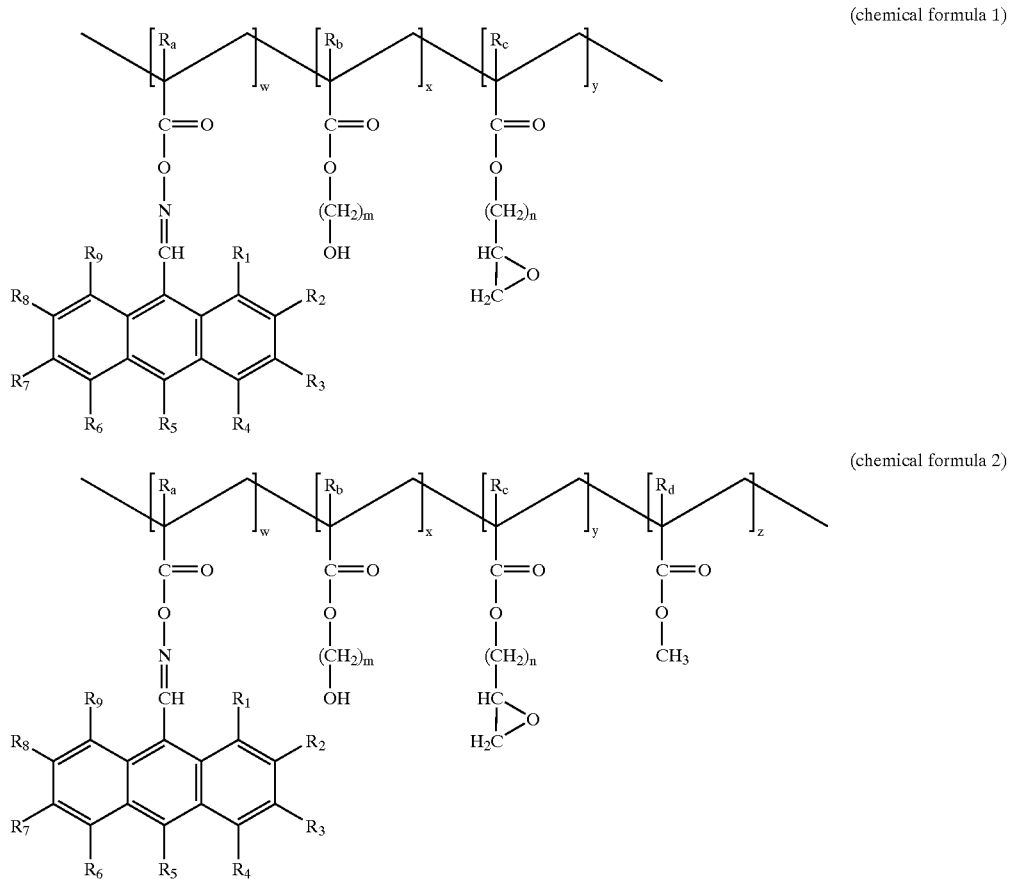

(chemical formula 1)

(chemical formula 2)

wherein,
$R_a$, $R_b$, $R_c$ $R_d$ each is hydrogen or a methyl group;
$R_1$ to $R_9$, which are the same or different, each represents hydrogen, hydroxy, methoxycarbonyl, carboxyl, hydroxymethyl or a substituted or unsubstituted, linear or branched $C_1$–$C_5$ alkyl or alkoxyalkyl;
w, x, y and z each is a mole fraction in the range from 0.01 to 0.99; and
m and n each is an integer of 1 to 5.

The polymers of the present invention are designed to show high absorbance at 193 nm and 248 nm wavelengths. To accomplish this result, a chromophore substituent which is able to absorb light at a wavelength of 193 nm as well as 248 nm is grafted to the backbone of the polymer.

The polymer of chemical formula 1 can be prepared by polymerizing a 9-anthraldehydeoximacrylate-type monomer, a hydroxy alkyl acrylate-type monomer, and a glycidyl acrylate-type monomer with the aid of an initiator in a solvent. Each of the monomers has a mole fraction ranging from 0.01 to 0.99, preferably 0.1 to 0.9.

The polymer of chemical formula 2 can be prepared by polymerizing a 9-anthraldehydeoximacrylate-type monomer, a hydroxy alkyl acrylate-type monomer, a glycidyl acrylate-type monomer and a methyl methacrylate-type monomer at a mole fraction of 0.01 to 0.99 for each monomer, preferably 0.1 to 0.9.

For initiating the polymerization reaction to prepare the polymers of the chemical formulas 1 and 2, ordinary radical initiators may be used, preferably one selected from the group consisting of 2,2-azobisisobutyronitrile (AIBN), acetylperoxide, laurylperoxide and t-butylperoxide. Also, ordinary solvents may be used for the polymerization, preferably a solvent selected from the group consisting of tetrahydrofuran, toluene, benzene, methylethyl ketone and dioxane.

Preferably, the polymerization of the polymers of chemical formulas 1 and 2 is carried out at 50°–90° C.

The present invention also pertains to an anti-reflective coating composition which comprises a polymer of chemical formula 1 or 2 in combination with at least one additive selected from the group consisting of the anthracene derivatives shown in Table 1, below:

TABLE 1
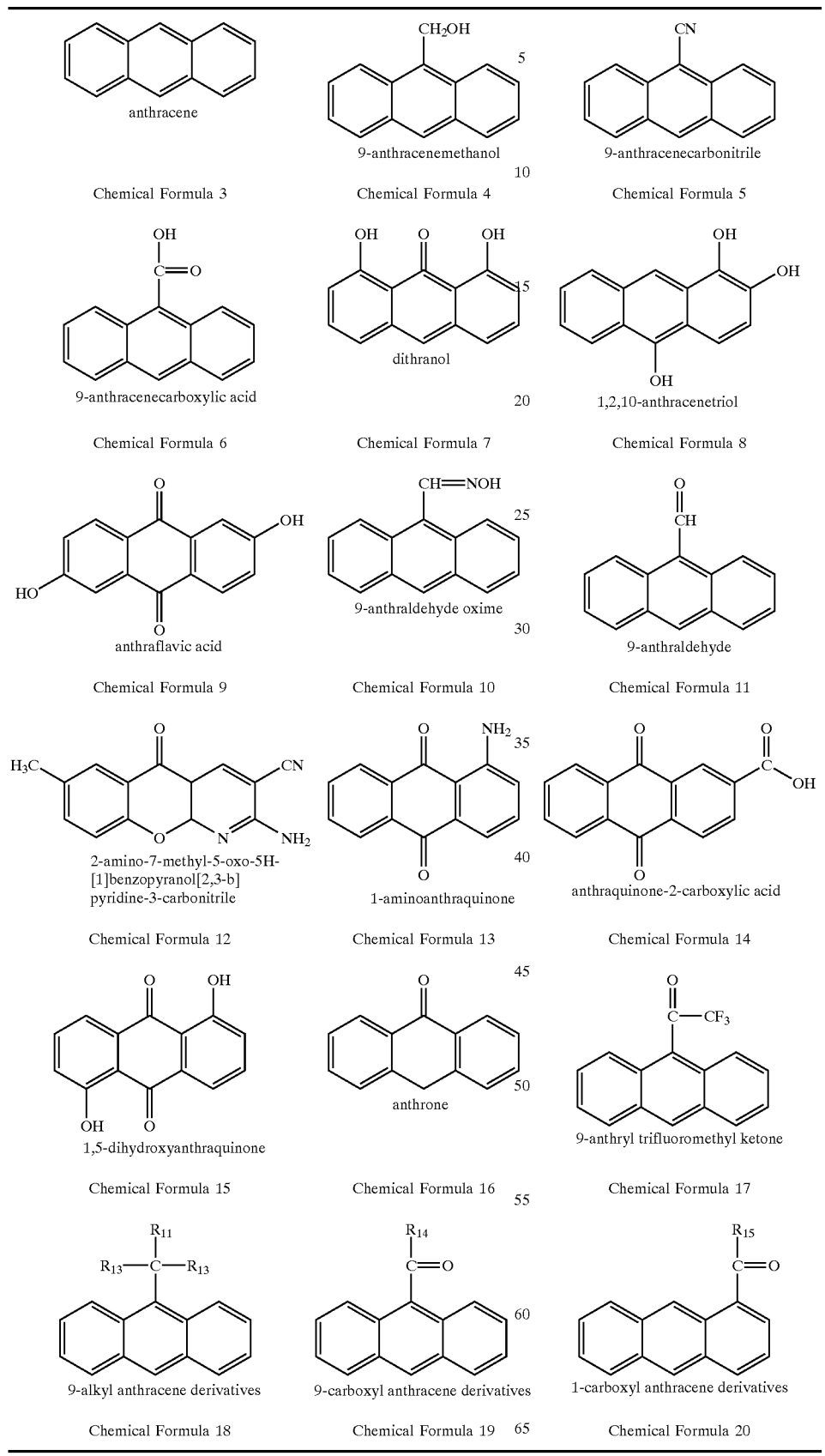

In Table 1, $R_{11}$, $R_{12}$, $R_{13}$, $R_{14}$ and $R_{15}$ independently represent hydrogen, hydroxy, hydroxymethyl, or substituted or unsubstituted linear or branched $C_1$–$C_5$ alkyl or alkoxyalkyl.

An anti-reflective coating composition according to the present invention may be prepared by adding a compound selected from Table 1, at an amount of 0.1 to 30% by weight, to a solution of a polymer of the chemical formula 1 or 2 in a solvent, and then filtering the resultant solution. This coating composition is applied on a wafer that is then hard-baked to form a cross-linked anti-reflective coating. Semiconductor devices can then be fabricated therefrom.

Ordinary organic solvents may be used in preparing the composition, with preference given to one selected from the group consisting of ethyl 3-ethoxy propionate, methyl 3-methoxy propionate, cyclohexanone and propyleneglycol methyletheracetate. The solvent is preferably used at an amount of 200 to 5000% by weight based on the weight of the anti-reflective coating polymer resin used.

It has been found that anti-reflective coatings of the present invention exhibit high performance in submicrolithographic processes using 248 nm KrF, 193 nm ArF and 157 nm $F_2$ lasers as light sources. The same is also true when electron beams, EUV (extremely ultraviolet) and ion beams are used as light sources.

The following examples are set forth to illustrate more clearly the principles and practice of this invention to one skilled in the art. As such, they are not intended to limit the invention, but are illustrative of certain preferred embodiments.

EXAMPLE 1

Synthesis of poly[9-anthraldehydeoximacrylate-(2-hydroxy ethylacrylate)-glycidylmethacrylate] copolymer Synthesis of 9-anthraldehydeoximacrylate 0.5 moles of 9-anthracenealdehydeoxim and 0.5 moles of pyridine are dissolved in tetrahydrofuran(THF) and then, 0.5 moles of acryloylchloride are added. After the completion of the reaction, the reaction solution is filtered, and extraction is conducted with ethyl acetate. The extract is washed many times with distilled water and dried by distillation under vacuum, to give 9-anthraldehydeoximacrylate, represented by the following chemical formula 21. The yield is 80%.

(chemical formula 21)

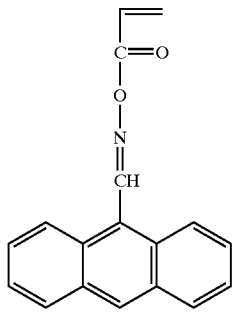

Synthesis of poly[9-anthraldehydeoximacrylate-(2-hydroxyethylacrylate)-glycidylmethacrylate] copolymer In a 500-ml round-bottom flask are placed 0.5 moles of the 9-anthraldehydeoximacrylate synthesized above, 0.3 moles of 2-hydroxyethylacrylate, and 0.2 moles of glycidylmethacrylate. This mixture is added to 300 g of separately prepared THF with stirring. Thereafter, in the presence of 0.1–3 g of 2,2'-azobisisobutyronitrile (AIBN), the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(2-hydroxyethylacrylate)-glycidylmethacrylate] copolymer, a polymer according to the present invention, represented by the following chemical formula 22. The yield is 81%.

(chemical formula 22)

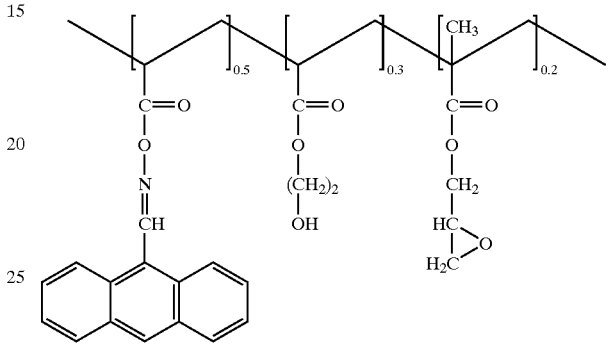

EXAMPLE II

Synthesis of poly[9-anthraldehydeoximacrylate-(3-hydroxypropylacrylate)-glycidylmethacrylate] copolymer In a 500-ml round-bottom flask are placed 0.5 moles of the 9-anthraldehydeoximacrylate synthesized in Example I, 0.3 moles of 3-hydroxypropylacrylate, and 0.2 moles of glycidylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(3-hydroxypropylacrylate)-glycidylmethacrylate] copolymer, a polymer according to the present invention, represented by the following chemical formula 23. The yield is 78%.

(chemical formula 23)

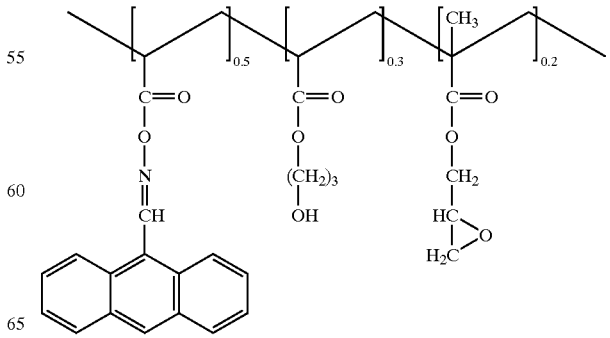

EXAMPLE III

Synthesis of poly[9-anthraldehydeoximacrylate-(2-hydroxyethylacrylate)-glycidylacrylate] copolymer In a 500-ml round-bottom flask are placed 0.5 moles of 9-anthraldehydeoxim acrylate, 0.3 moles of 2-hydroxyethylacrylate, and 0.2 moles of glycidylacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitates is filtered and dried to produce a poly[9-anthraldehydeoximacrylate-(2-hydroxyethylacrylate)-glycidylacrylate] copolymer, a polymer according to the present invention, represented by the following chemical formula 24. The yield is 80%.

(chemical formula 24)

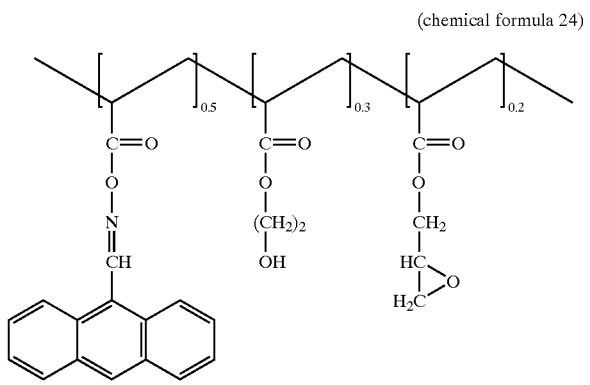

EXAMPLE IV

Synthesis of poly[9-anthraldehydeoximacrylate-(3-hydroxypropylacrylate)-glycidylacrylate] copolymer In a 500-ml round-bottom flask are placed 0.5 moles of 9-anthraldehydeoximacrylate, 0.3 moles of 3-hydroxypropylacrylate, and 0.2 moles of glycidylacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(3-hydroxypropylacrylate)-glycidylacrylate] copolymer, a polymer according to the present invention, represented by the following chemical formula 25. The yield is 80%.

(chemical formula 25)

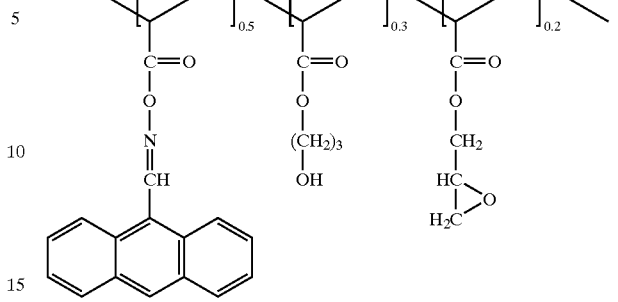

EXAMPLE V

Synthesis of poly[9-anthraldehydeoximacrylate-(4-hydroxybutylacrylate)-glycidylacrylate] copolymer In a 500-ml round-bottom flask are placed 0.5 moles of 9-anthraldehydeoxim acrylate, 0.3 moles of 4-hydroxybutylacrylate, and 0.2 moles of glycidylacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(4-hydroxybutylacrylate)-glycidylacrylate] copolymer, a polymer according to the present invention, represented by the following chemical formula 26. The yield is 81%.

(chemical formula 26)

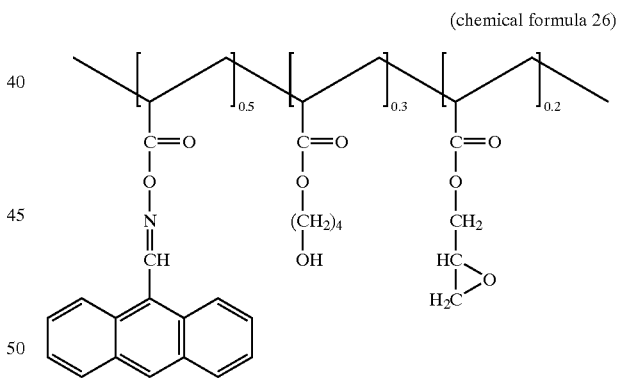

EXAMPLE VI

Synthesis of poly[9-anthraldehydeoxim methacrylate-(2-hydroxyethyl acrylate)-glycidylmethacrylate] copolymer Synthesis of 9-anthraldehydeoximmethacrylate 0.5 moles of 9-anthracene aldehydeoxim and 0.5 moles of pyridine are dissolved in THF and then, 0.5 moles of methacryloyl chloride are added. After completion of the reaction, this reaction solution is filtered, and extraction is conducted with ethyl acetate. The extract is washed many times with distilled water and dried by distillation under vacuum, to give 9-anthraldehydeoximmethacrylate, represented by the following chemical formula 27. The yield is 82%.

(chemical formula 27)

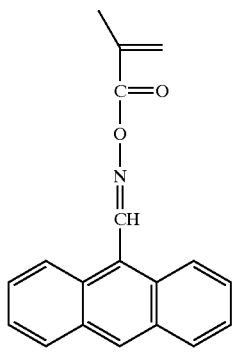

Synthesis of poly[9-anthraldehydeoximmethacrylate-(2-hydroxyethylacrylate)-glycidylmethacrylate] copolymer In a 500-ml round-bottom flask are placed 0.5 moles of the 9-anthraldehydeoximmethacrylate synthesized above, 0.3 moles of 2-hydroxyethylacrylate, and 0.2 moles of glycidylmethacrylate. This mixture is added to 300 g of separately prepared THF with stirring. Thereafter, in the presence of 0.1–3 g of 2,2'-azobisisobutyronitrile (AIBN), the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(2-hydroxyethylacrylate)-glycidylmethacrylate] copolymer, a polymer according to the present invention, represented by the following chemical formula 28. The yield is 78%.

(chemical formula 28)

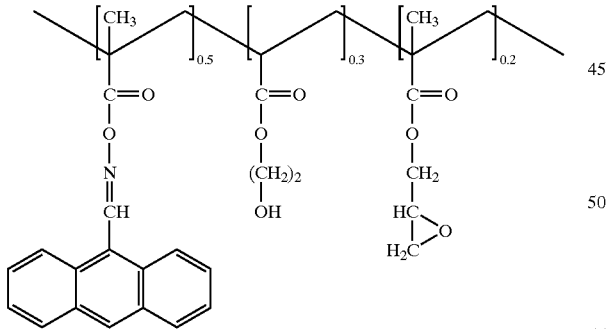

EXAMPLE VII

Synthesis of poly[9-anthraldehydeoximmethacrylate-(3-hydroxypropyl acrylate)-glycidylmethacrylate] copolymer In a 500-ml round-bottom flask are placed 0.5 moles of the 9-anthraldehydeoximmethacrylate synthesized in Example VI, 0.3 moles of 3-hydroxypropylacrylate, and 0.2 moles of glycidylmethacrylate. This mixture is added to 300 g of separately prepared THF with stirring, after which, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(3-hydroxypropylacrylate)-glycidylmethacrylate] copolymer, a polymer according to the present invention, represented by the following chemical formula 29. The yield is 81%.

(chemical formula 29)

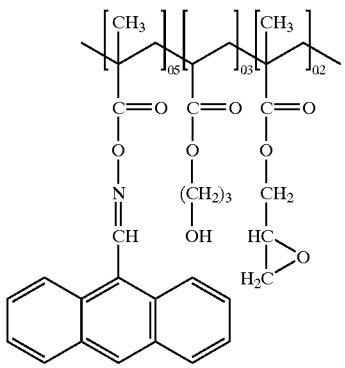

EXAMPLE VIII

Synthesis of poly[9-anthraldehydeoximmethacrylate-(4-hydroxybutyl acrylate)-glycidylmethacrylate] copolymer In a 500-ml round-bottom flask are placed 0.5 moles of the 9-anthraldehydeoximmethacrylate, 0.3 moles of 4-hydroxybutylacrylate and, 0.2 moles of glycidylmethacrylate. This mixture is added to 300 g of separately prepared THF with stirring, after which, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(4-hydroxybutylacrylate)-glycidylmethacrylate] copolymer, a polymer according to the present invention, represented by the following chemical formula 30. The yield is 80%.

(chemical formula 30)

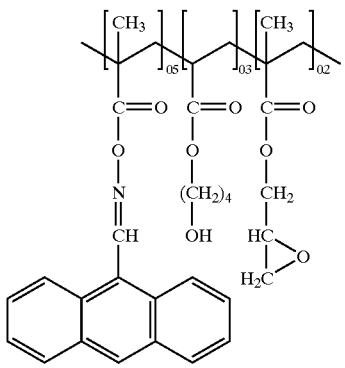

EXAMPLE IX

Synthesis of poly[9-anthraldehydeoximmethacrylate-(2-hydroxyethyl acrylate)-glycidylacrylate] copolymer In a 500-ml round-bottom flask are placed 0.5 moles of the 9-anthraldehyde oximmethacrylate, 0.3 moles of 2-hydroxyethylacrylate, and 0.2 moles of glycidylacrylate. This mixture is added to 300 g of separately prepared THF with stirring, after which, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(2-hydroxyethylacrylate)-glycidylacrylate] copolymer, a polymer according to the present invention, represented by the following chemical formula 31. The yield is 78%.

(chemical formula 31)

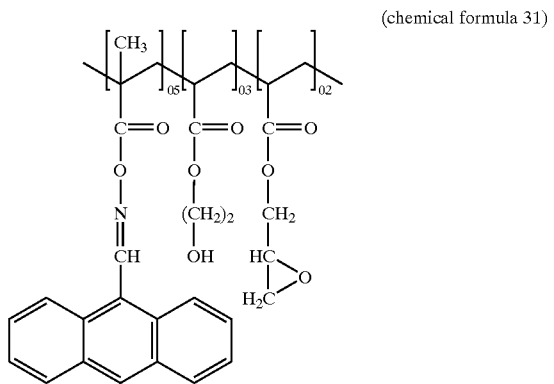

EXAMPLE X

Synthesis of poly[9-anthraldehydeoximmethacrylate-(3-hydroxypropyl acrylate)-glycidylacrylate] copolymer In a 500-ml round-bottom flask are placed 0.5 moles of the 9-anthraldehyde oximmethacrylate, 0.3 moles of 3-hydroxypropylacrylate, and 0.2 moles of glycidylacrylate. This mixture is added to 300 g of separately prepared THF with stirring, after which, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(3-hydroxypropylacrylate)-glycidylacrylate] copolymer, a polymer according to the present invention, represented by the following chemical formula 32. The yield is 80%.

(chemical formula 32)

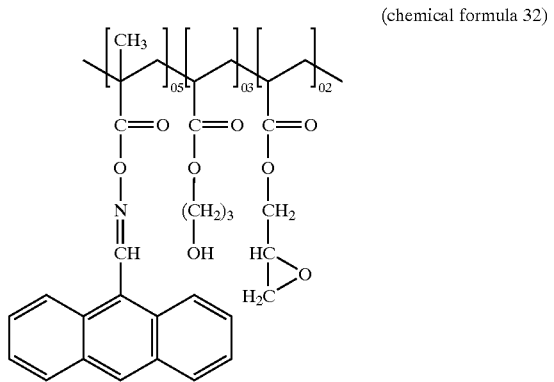

EXAMPLE XI

Synthesis of poly[9-anthraldehydeoximmethacrylate-(4-hydroxybutyl acrylate)-glycidylacrylate] copolymer In a 500-ml round-bottom flask are placed 0.5 moles of the 9-anthraldehydeoximmethacrylate, 0.3 moles of 4-hydroxybutylacrylate, and 0.2 moles of glycidylacrylate. This mixture is added to 300 g of separately prepared THF with stirring, after which, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(4-hydroxybutylacrylate)-glycidylacrylate] copolymer, a polymer according to the present invention, represented by the following chemical formula 33. The yield is 80%.

(chemical formula 33)

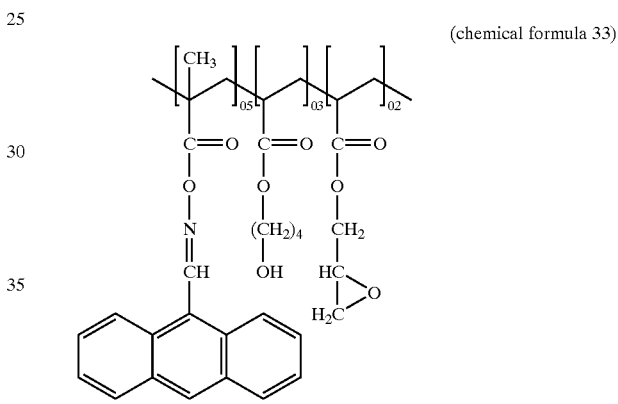

EXAMPLE XII

Synthesis of poly[9-anthraldehydeoximacrylate-(2-hydroxyethylacrylate)-glycidylmethacrylate-methylmethacrylate] copolymer In a 500-ml round-bottom flask are placed 0.3 moles of 9-anthraldehydeoximacrylate, 0.3 moles of 2-hydroxyethylacrylate, 0.2 moles of glycidylmethacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(2-hydroxyethylacrylate)-glycidylmethacrylate-methylmethacrylate] copolymer, a polymer according to the present invention, represented by the following chemical formula 34. The yield is 80%.

(chemical formula 34)

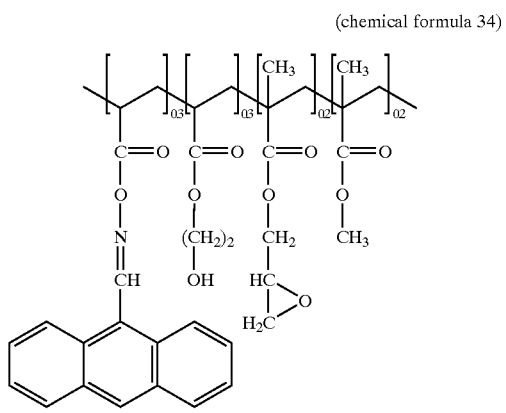

EXAMPLE XIII

Synthesis of poly[9-anthraldehydeoximacrylate-(3-hydroxypropylacrylate)-glycidylmethacrylate-methylmethacrylate] copolymer In a 500-ml round-bottom flask are placed 0.3 moles of 9-anthraldehydeoximacrylate, 0.3 moles of 3-hydroxypropylacrylate, 0.2 moles of glycidylmethacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(3-hydroxypropylacrylate)-glycidylmethacrylate-methylmethacrylate] copolymer, a polymer according to the present invention, represented by the following chemical formula 35. The yield is 79%.

(chemical formula 35)

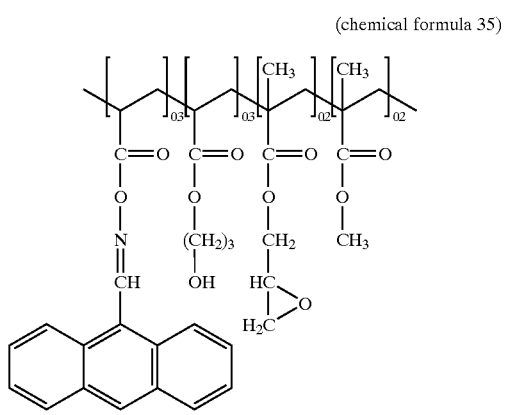

EXAMPLE XIV

Synthesis of poly[9-anthraldehydeoximacrylate-(2-hydroxyethylacrylate)-glycidylacrylate-methylmethacrylate] copolymer In a 500-ml round-bottom flask are placed 0.3 moles of 9-anthraldehydeoximacrylate, 0.3 moles of 2-hydroxyethylacrylate, 0.2 moles of glycidylacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(2-hydroxyethylacrylate)-glycidylacrylate-methylmethacrylate] copolymer, a polymer according to the present invention, represented by the following chemical formula 36. The yield is 81%.

(chemical formula 36)

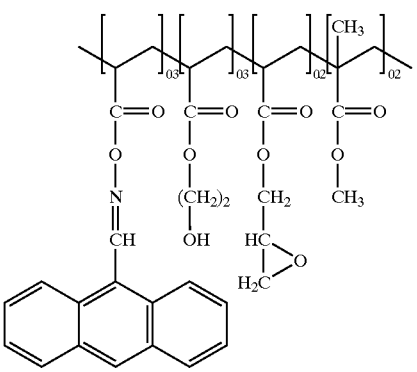

EXAMPLE XV

Synthesis of poly[9-anthraldehydeoximacrylate-(3-hydroxypropylacrylate)-glycidylacrylate-methylmethacrylate] copolymer In a 500-ml round-bottom flask are placed 0.3 moles of 9-anthraldehydeoximacrylate, 0.3 moles of 3-hydroxypropylacrylate, 0.2 moles of glycidylacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(3-hydroxypropylacrylate)-glycidylacrylate-methylmethacrylate] copolymer, a polymer according to the present invention, represented by the following chemical formula 37. The yield is 79%.

(chemical formula 37)

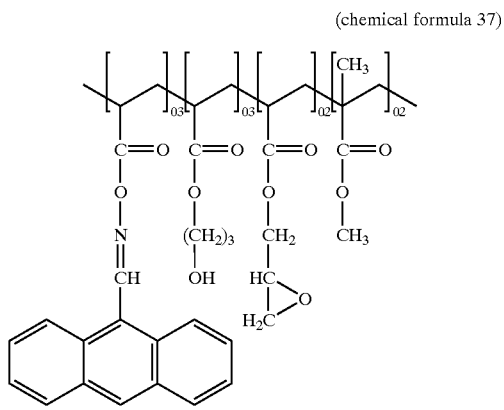

EXAMPLE XVI

Synthesis of poly[-9-anthraldehydeoximacrylate-(4-hydroxybutylacrylate)-glycidylacrylate-methylmethacrylate] copolymer In a 500-ml round-bottom flask are placed 0.3 moles of 9-anthraldehydeoximacrylate, 0.3 moles of 4-hydroxybutylacrylate, 0.2 moles of glycidylacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximacrylate-(4-hydroxybutylacrylate)-glycidylacrylate-methylmethacrylate] copolymer, a polymer according to the present invention, represented by the following chemical formula 38. The yield is 80%.

(chemical formula 38)

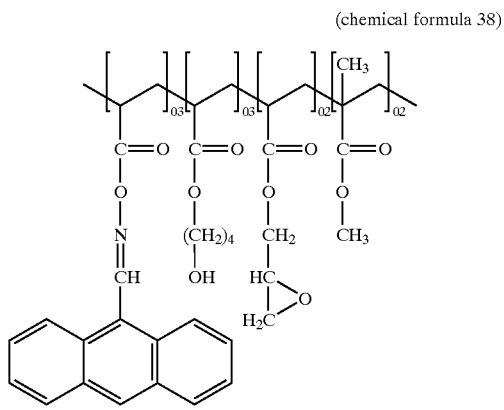

EXAMPLE XVII

Synthesis of poly[9-anthraldehydeoximmethacrylate-(2-hydroxyethylacrylate)-glycidylmethacrylate-methylmethacrylate] copolymer In a 500-ml round-bottom flask are placed 0.3 moles of 9-anthraldehydeoximmethacrylate, 0.3 moles of 2-hydroxyethylacrylate, 0.2 moles of glycidylmethacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(2-hydroxyethylacrylate)-glycidylmethacrylate-methylmethacrylate] copolymer, a polymer according to the present invention, represented by the following chemical formula 39. The yield is 80%.

(chemical formula 39)

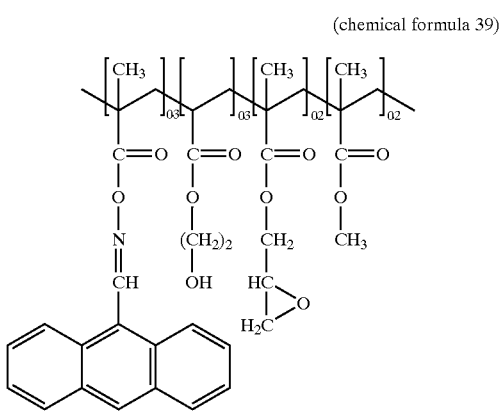

EXAMPLE XVIII

Synthesis of poly[9-anthraldehydeoximmethacrylate-(3-hydroxypropylacrylate)-glycidylmethacrylate-methylmethacrylate] copolymer In a 500-ml round-bottom flask are placed 0.3 moles of 9-anthraldehydeoximmethacrylate, 0.3 moles of 3-hydroxypropylacrylate, 0.2 moles of glycidylmethacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(3-hydroxypropylacrylate)-glycidylmethacrylate-methylmethacrylate] copolymer, a polymer according to the present invention, represented by the following chemical formula 40. The yield is 78%.

(chemical formula 40)

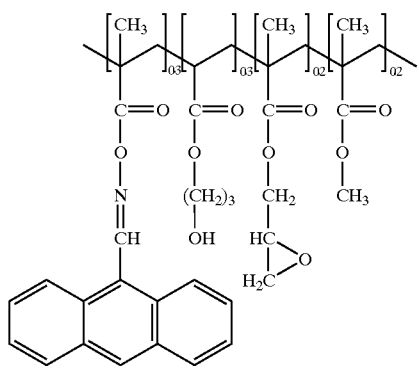

EXAMPLE XIX

Synthesis of poly[9-anthraldehydeoximmethacrylate-(4-hydroxybutylacrylate)-glycidylmethacrylate-methylmethacrylate] copolymer In a 500-ml round-bottom flask are placed 0.3 moles of 9-anthraldehydeoximmethacrylate, 0.3 moles of 4-hydroxybutylacrylate, 0.2 moles of glycidylmethacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(4-hydroxybutylacrylate)-glycidylmethacrylate-methylmethacrylate] copolymer, a polymer according to the present invention, represented by the following chemical formula 41. The yield is 81%.

(chemical formula 41)

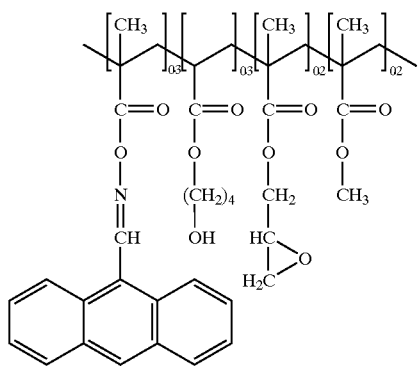

EXAMPLE XX

Synthesis of poly[9-anthraldehydeoximmethacrylate-(2-hydroxyethylacrylate)-glycidylacrylate-methylmethacrylate] copolymer In a 500-ml round-bottom flask are placed 0.3 moles of 9-anthraldehydeoximmethacrylate, 0.3 moles of 2-hydroxyethylacrylate, 0.2 moles of glycidylacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(2-hydroxyethylacrylate)-glycidylacrylate-methylmethacrylate] copolymer, a polymer according to the present invention, represented by the following chemical formula 42. The yield is 79%.

(chemical formula 42)

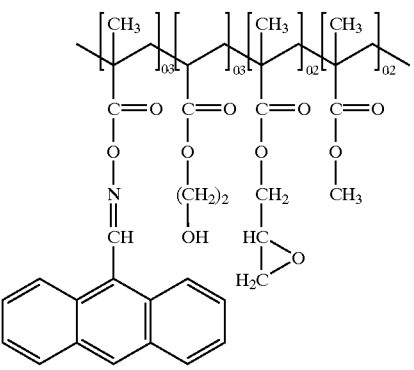

EXAMPLE XXI

Synthesis of poly[9-anthraldehydeoximmethacrylate-(3-hydroxypropylacrylate)-glycidylacrlyate-methylmethacrylate] copolymer In a 500-ml round-bottom flask are placed 0.3 moles of 9-anthraldehydeoximmethacrylate, 0.3 moles of 3-hydroxypropylacrylate, 0.2 moles of glycidylacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(3-hydroxypropyllacrylate)-glycidylacrylate-methylmethacrylate] copolymer, a polymer according to the present invention, represented by the following chemical formula 43. The yield is 81%.

(chemical formula 43)

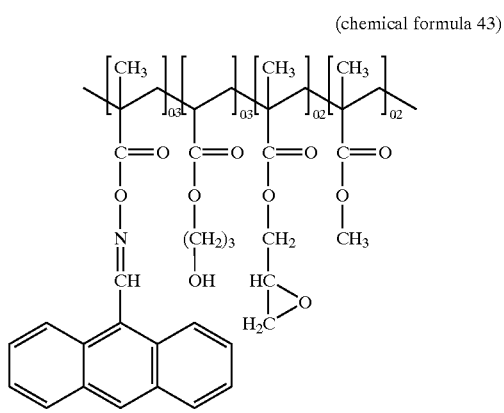

EXAMPLE XXII

Synthesis of poly[9-anthraldehydeoximmethacrylate-(4-hydroxybutylacrylate)-glycidylacrylate-methylmethacrylate] copolymer In a 500-ml round-bottom flask are placed 0.3 moles of 9-anthraldehydeoximmethacrylate, 0.3 moles of 4-hydroxybutylacrylate, 0.2 moles of glycidylacrylate, and 0.2 moles of methylmethacrylate. This mixture is added to 300 g of separately prepared THF with stirring. Thereafter, in the presence of 0.1–3 g of AIBN, the reaction solution is subjected to polymerization at 60°–75° C. for 5–20 hours in a nitrogen atmosphere. After completion of the polymerization, the solution is precipitated in ethyl ether or normal-hexane and the precipitate is filtered and dried to produce a poly[9-anthraldehydeoximmethacrylate-(4-hydroxybutylacrylate)-glycidylacrylate-methylmethacrylate] copolymer, a polymer according to the present invention, represented by the following chemical formula 44. The yield is 80%.

(chemical formula 44)

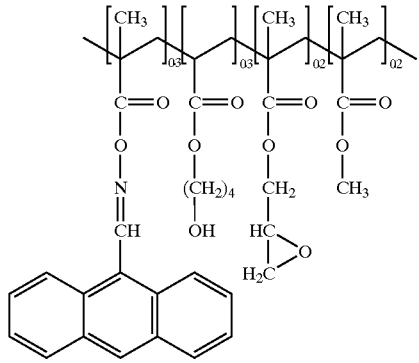

EXAMPLE XXIII

Preparation of Anti-Reflective Coating

In 200–5,000% by weight of propyleneglycol methylether acetate (PGMEA) are dissolved a resin having a chemical structure of chemical formula 1 or 2, obtained in any of Examples I to XXII. This solution, alone or in combination with 0.1–30% by weight of at least one additive selected from the compounds of chemical formulas 3 to 20 in Table 1, is filtered, coated on a wafer, and hard-baked at 100°–300° C. for 10–1,000 sec. On the anti-reflective coating thus formed, a photosensitive material may be applied and imaged to form ultrafine patterns in the conventional manner.

As described hereinbefore, the anti-reflective coatings of the present invention, which are obtained from a polymer resin of chemical formula 1 or 2, alone or in combination with an additive of one of the chemical formulas 3 to 20, contains chromophore substituents sufficient to exhibit absorbance at the wavelengths useful for submicrolithography. Thus, the anti-reflective coatings of the present invention can play an excellent role in forming ultrafine patterns. For example, these ARCs can prevent the back reflection from lower layers of the semiconductor element, as well as eliminate standing waves caused by light and thickness changes of the photoresist itself during a submicrolithographic process using a 248 nm KrF, 193 nm ArF or 157 nm $F_2$ laser. This results in the stable formation of ultrafine patterns suitable for 64M, 256M, 1 G, 4 G and 16 G DRAM semiconductor devices and a great improvement in the production yield.

Although the invention has been described in detail by referring to certain preferred embodiments, it will be understood that various modifications can be made within the spirit and scope of the invention. The invention is not to be limited except as set forth in the following claims.

What is claimed is:

1. 9-Anthraldehydeoximacrylate, represented by the following chemical formula 21:

(chemical formula 21)

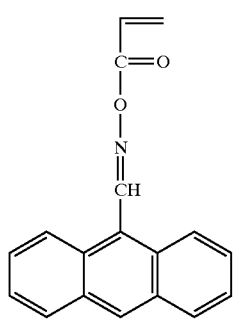

2. A method for preparing 9-anthraldehydeoximacrylate comprising reacting 9-anthracenealdehydeoxime with acryloylchloride.

3. 9-Anthraldehydeoximmethacrylate, represented by following chemical formula 27:

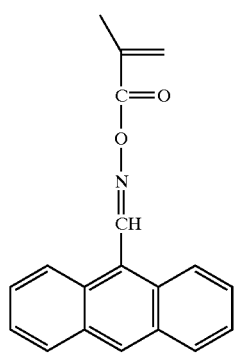

(chemical formula 27)

4. A method for preparing 9-anthraldehydeoximmethacylate comprising reacting 9-anthracenealdehydeoxime with methacryloyl chloride.

5. The method of claim 2, wherein the reaction is carried out in the presence of a base.

6. The method of claim 5, wherein the base is pyridine.

7. The method of claim 5, wherein the reaction is carried out in the presence of an organic solvent.

8. The method of claim 7, wherein the organic solvent is tetrahydrofuran.

9. The method of claim 4, wherein the reaction is carried out in the presence of a base.

10. The method of claim 9, wherein the base is pyridine.

11. The method of claim 9, wherein the reaction is carried out in the presence of an organic solvent.

12. The method of claim 11, wherein the organic solvent is tetrahydrofuran.

* * * * *

UNITED STATES PATENT AND TRADEMARK OFFICE
CERTIFICATE OF CORRECTION

PATENT NO. : 6,538,090 B2
DATED : March 25, 2003
INVENTOR(S) : Min Ho Jung, Sung-eun Hong and Ki Ho Baik It is certified that error appears in the above-identified patent and that said Letters Patent is hereby corrected as shown below:

Column 5,
Lines 55-65, in Table 1, please replace chemical formula 18 with the following chemical formula 18:

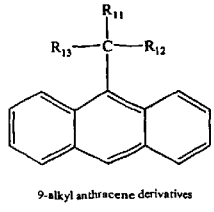

Column 12,
Lines 10-25, please replace chemical formula 29 with the following chemical formula 29:

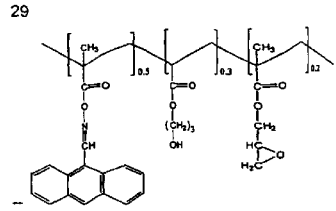

(chemical formula 29) --.

Lines 45-60, please replace chemical formula 30 with the following chemical formula 30:

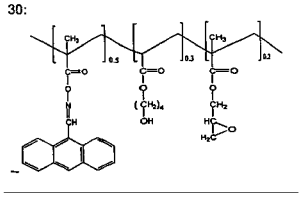

(chemical formula 30) --.

Column 13,
Lines 15-30, please replace chemical formula 31 with the following chemical formula 31:

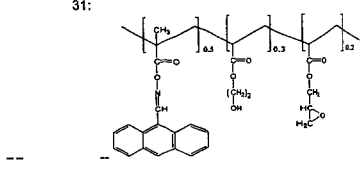

(chemical formula 31) --.

UNITED STATES PATENT AND TRADEMARK OFFICE
CERTIFICATE OF CORRECTION

PATENT NO. : 6,538,090 B2  
DATED : March 25, 2003  
INVENTOR(S) : Min Ho Jung, Sung-eun Hong and Ki Ho Baik It is certified that error appears in the above-identified patent and that said Letters Patent is hereby corrected as shown below:

Column 13,  
Lines 51-65, please replace chemical formula 32 with the following chemical formula 32:

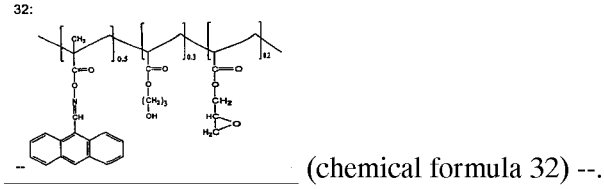

(chemical formula 32) --.

Column 14,  
Lines 25-40, please replace chemical formula 33 with the following chemical formula 33:

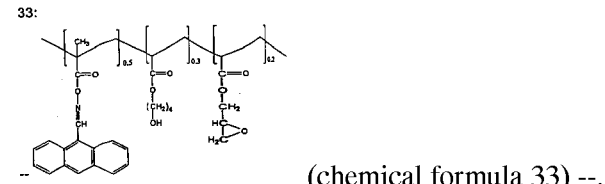

(chemical formula 33) --.

Column 15,  
Lines 1-20, please replace chemical formula 34 with the following chemical formula 34:

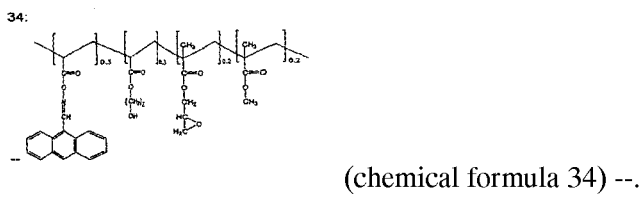

(chemical formula 34) --.

Lines 45-60, please replace chemical formula 35 with the following chemical formula 35:

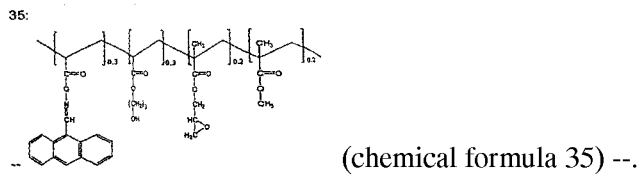

(chemical formula 35) --.

Column 16,  
Lines 20-35, please replace chemical formula 36 with the following chemical formula 36:

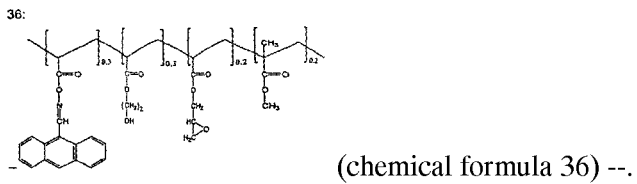

(chemical formula 36) --.

UNITED STATES PATENT AND TRADEMARK OFFICE
CERTIFICATE OF CORRECTION

PATENT NO. : 6,538,090 B2  
DATED : March 25, 2003  
INVENTOR(S) : Min Ho Jung, Sung-eun Hong and Ki Ho Baik Page 3 of 4

It is certified that error appears in the above-identified patent and that said Letters Patent is hereby corrected as shown below:

Column 17,  
Lines 1-20, please replace chemical formula 37 with the following chemical formula 37:

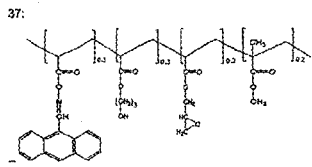

(chemical formula 37) --.

Lines 45-60, please replace chemical formula 38 with the following chemical formula 38:

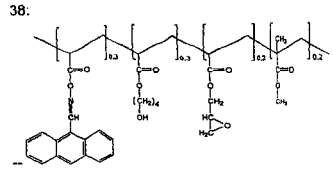

(chemical formula 38) --.

Column 18,  
Lines 20-35, please replace chemical formula 39 with the following chemical formula 39:

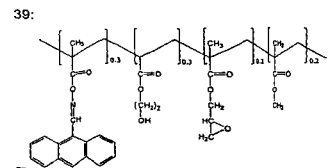

(chemical formula 39) --.

Column 19,  
Lines 1-20, please replace chemical formula 40 with the following chemical formula 40:

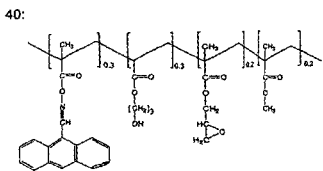

(chemical formula 40) --.

Lines 43-58, please replace chemical formula 41 with the following chemical formula 41:

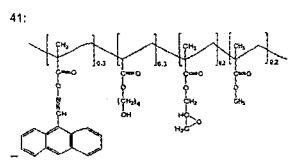

(chemical formula 41) --.

UNITED STATES PATENT AND TRADEMARK OFFICE
CERTIFICATE OF CORRECTION

PATENT NO.   : 6,538,090 B2
DATED        : March 25, 2003
INVENTOR(S)  : Min Ho Jung, Sung-eun Hong and Ki Ho Baik It is certified that error appears in the above-identified patent and that said Letters Patent is hereby corrected as shown below:

Column 20,
Lines 19-33, please replace chemical formula 42 with the following chemical formula 42:

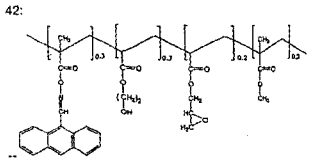

(chemical formula 42) --.

Column 21,
Lines 1-20, please replace chemical formula 43 with the following chemical formula 43:

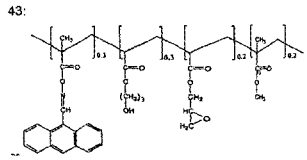

(chemical formula 43) --.

Lines 45-60, please replace chemical formula 44 with the following chemical formula 44:

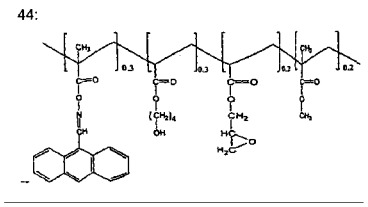

(chemical formula 44) --.

Signed and Sealed this

Twenty-fourth Day of August, 2004

JON W. DUDAS
*Director of the United States Patent and Trademark Office*